United States Patent [19]

Saari

[11] Patent Number: 4,483,858
[45] Date of Patent: Nov. 20, 1984

[54] 8-[2-IMIDAZOLYLMETHYLOXY(THIO, OR AMINO)]-IMIDAZO[1,2-a]PYRAZINES AND DERIVATIVES FOR TREATING HYPERTENSION

[75] Inventor: Walfred S. Saari, Lansdale, Pa.

[73] Assignee: Merck & Co., Inc., Rahway, N.J.

[21] Appl. No.: 436,753

[22] Filed: Oct. 25, 1982

[51] Int. Cl.$^3$ .................. C07D 487/04; A61K 31/495
[52] U.S. Cl. ...................................... 424/250; 544/350
[58] Field of Search ......................... 544/350; 424/250

[56] References Cited

U.S. PATENT DOCUMENTS 4,242,344 12/1980 Lumma ................................ 544/350

Primary Examiner—Mark L. Berch
Attorney, Agent, or Firm—William H. Nicholson

[57] ABSTRACT

8-[2-Imidazolylmethyloxy(thio, or amino)]-imidazo[1,2-a]pyrazines and derivatives and acid addition salts thereof are central adrenergic receptor agonists and thereby useful as antihypertensives.

9 Claims, No Drawings

8-[2-IMIDAZOLYLMETHYLOXY(THIO, OR AMINO)]-IMIDAZO[1,2-a]PYRAZINES AND DERIVATIVES FOR TREATING HYPERTENSION

BACKGROUND OF THE INVENTION

This invention is concerned with novel 8-[2-imidazolylmethyloxy(thio, or amino)]imidazo[1,2-a]pyrazines and derivatives or pharmaceutically acceptable salts thereof of structural Formula I

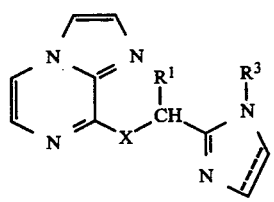

which have antihypertensive activity. It also relates to a process for preparing the novel compounds, pharmaceutical compositions comprising the novel compounds and to a method of treating hypertension with the novel compounds.

The imidazo[1,2-a]pyrazine group is known in compounds with useful pharmacological properties, such as the piperazinyl-imidazo[1,2-a]pyrazines of U.S. Pat. No. 4,242,344 which are anorexigenic, antihypertensive, analgesic, antiarrhythmic and antidepressant agents.

Now, with the present invention there is provided a group of substituted imidazo[1,2-a]pyrazines of structural Formula I which are antihypertensive agents by virtue of their ability to stimulate central adrenergic receptor sites.

DETAILED DESCRIPTION OF THE INVENTION

This invention is concerned with compounds of structural formula I:

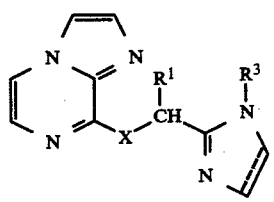

or a pharmaceutically acceptable salt thereof, wherein X is

—S—, ¢SO, ¢SO$_2$, or —O—; and
$R^1$, $R^2$ and $R^3$ are independently hydrogen or $C_{1-3}$ alkyl;
and the dotted line is an optional double bond.

The pharmaceutically acceptable salts coming within the purview of this invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric tartaric, citric, acetic, benzoic, 2-acetoxybenzoic, salicylic, succinic acid, theophylline, 8-chlorotheophylline, p-aminobenzoic, p-acetamidobenzoic, methanesulfonic, or ethane disulfonic.

The novel compounds of this invention are prepared in accordance with the following general Reaction Scheme I:

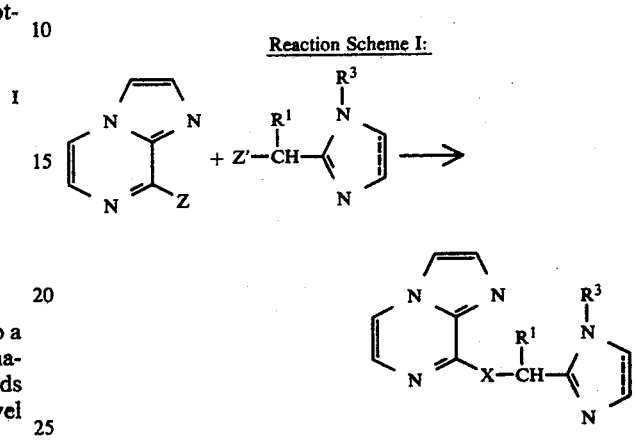

wherein Z and Z' are XH and Y respectively or Z and Z' are Y and XH respectively.

More specifically, the process is represented by Reaction Scheme Ia or Ib.

wherein $R^1$ is as previously defined, X is $NR^2$, —S— or —O— and Y is halogen, especially chloro, $C_{1-5}$alkylsulfonyloxy, such as methanesulfonyloxy; or benzenoid arylsulfonyloxy, such as benzenesulfonyloxy or toluenesulfonyloxy.

The reaction is conducted in an inert organic solvent such as a $C_{1-4}$alkanol, preferably methanol, or acetonitrile, dimethylformamide, dimethylsulfoxide or hexamethylphosphoramide, in the presence of a strong base such as an alkali metal hydride or alkali metal $C_{1-4}$alkoxide, for example sodium hydride or potassium tert-butoxide.

There are employed temperatures ranging from about 15° C. to about 100° C., preferably under anhydrous conditions until a substantial amount of desired compound of Formula I is obtained, typically for a period of from about 2 to about 24 hours, preferably from about 3 to 20 hours.

Those compounds wherein X is —S— are readily oxidized by well known chemical reactions to the analogs wherein X is >SO or >$SO_2$.

In the novel method of treating hypertension a novel compound or pharmaceutically acceptable salt thereof is administered in an amount ranging from about 0.01 to about 20 mg per kg of body weight per day, preferably from about 0.1 to about 10 mg per kg of body weight per day in a single dose or in 2 to 4 divided doses.

The compounds, or pharmaceutically acceptable salts thereof, of the present invention, in the described dosages, are administered orally, intraperitoneally, subcutaneously, intramuscularly, or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions, or preparations is such that a suitable dosage will be obtained.

The following examples illustrate the present invention without, however, limiting the same thereto.

EXAMPLE 1

8-(4,5-Dihydro-1H-imidazol-2-ylmethylthio)imidazo[1,2-a]pyrazine dihydrochloride

Step A: Preparation of 8-mercaptoimidazo[1,2-a]pyrazine

To 3.10 g (0.02 mol) of 8-chloroimidazo[1,2-a]pyrazine in 70 ml of ethanol was added 1.52 g (0.02 mol) of thiourea and the mixture was refluxed. After 3 hours, the reaction mixture was cooled to 0° C. The thiouronium salt was collected by filtration, dried and suspended in 80 ml of water. To this was added 3.46 g (33 mmol) of sodium carbonate. The reaction mixture was stirred for 15 minutes and then diluted with 30 ml of 5% sodium hydroxide solution. The aqueous solution was washed with 50 ml of chloroform, made acidic with acetic acid and then extracted with 2×50 ml of chloroform. The organic extracts were dried ($Na_2SO_4$), filtered, and concentrated to yield the crystalline product.

Step B: Preparation of 8-(4,5-dihydro-1H-imidazol-2-ylmethylthio)imidazo[1,2-a]pyrazine dihydrochloride To 30 ml of methanol was added 0.230 g (10.0 mmol) of sodium metal. After 30 minutes, 750 mg (5.0 mmol) of 8-mercaptoimidazo[1,2-a]pyrazine was added followed by the addition of 750 mg (5.0 mmol) of 2-(chloromethyl)-4,5-dihydroimidazole hydrochloride. The mixture was stirred at room temperature for 18 hours. The precipitated sodium chloride was removed by filtration, and the filtrate was evaporated to dryness. The oily residue was then dissolved in 50 ml of chloroform and extracted with 2×40 ml of 5% NaOH solution, dried ($Na_2SO_4$), filtered and concentrated. The resulting product was purified by flash chromatography (230–400 mesh $SiO_2$, 10% MeOH/$CHCl_3$ saturated with $NH_3$) to give the product which was dissolved in ethanolic HCl. Excess ether was added and the precipitate was collected, to give the dihydrochloride salt of the product, m.p. 207°–210° C.

EXAMPLE 2

8-(1-methyl-1H-imidazol-2-ylmethylthio)imidazo[1,2-a]pyrazine hydrogen maleate

To a solution of 2.02 g (20 mmol) of triethylamine in 30 ml of absolute ethanol was added 1.52 g (10 mmol) of 8-mercaptoimidazo[1,2-a]pyrazine. After stirring for 30 minutes at room temperature, 1.67 g (10 mmol) of 2-chloromethyl-N-methylimidazole hydrochloride was added in one portion. The reaction mixture was stirred for 20 hours and then poured into 50 ml of 5% NaOH. The product was extracted into 2×70 ml of chloroform, dried ($Na_2SO_4$), filtered, and concentrated. The oily residue was purified by flash chromatography (230–400 mesh $SiO_2$, 5% MeOH/$CHCl_3$ saturated with $NH_3$ as eluent) and the resultant product was mixed with maleic acid in acetone and ether to give the hydrogen maleate salt of the product, m.p. 148.5°–150° C.

EXAMPLE 3

8-(4,5-Dihydro-1H-imidazol-2-ylmethoxy)imidazo[1,2-a]pyrazine dihydrochloride hemihydrate To a slurry of 530 mg (22 mmol) of pentane-washed sodium hydride in 50 ml of dry dimethylformamide (DMF) was added 1.37 g (10.0 mmol) of 2-hydroxymethyl)-4,5-dihydroimidazole hydrochloride. After 30 minutes at room temperature, 1.55 g (10.0 mmol) of 8-chloroimidazo[1,2-a]pyrazine in 30 ml of DMF was added dropwise. After 1 hour at room temperature, the mixture was concentrated to dryness. The residue was dissolved in 30 ml of water and extracted with 2×50 ml of chloroform. The combined organic extracts were dried ($Na_2SO_4$), filtered, and concentrated. The oily residue was purified by flash chromatography (230–400 mesh $SiO_2$; 10% MeOH/$CHCl_3$ saturated with $NH_3$ as eluent) to afford the product. Treatment with ethanolic HCl and excess diethyl ether afforded the crystalline dihydrochloride hemihydrate salt of the product, m.p. 162°–165° C. (dec).

EXAMPLE 4

N-(4,5-Dihydro-1H-imidazol-2-ylmethyl)-N-methyl-8-aminoimidazo[1,2-a]pyrazine hydrogen oxalate

Step A: Preparation of Ethyl N-benzyloxycarbonyl-N-methylaminoacetimidate hydrochloride Methylaminoacetonitrile hydrochloride (6.9 g; 0.065 mol) and benzyl chloroformate (11.0 g; 0.065 mol) were mixed and cooled to 0° C. in an ice bath. Sodium hydroxide solution (10%, 65 ml) was added dropwise, maintaining the temperature below 10° C. After stirring the reaction an additional hour at 0° C., the two-phase mixture was extracted with methylene chloride. The organic extracts were washed with water and brine and dried (Na$_2$SO$_4$). Removal of the methylene chloride afforded N-benzyloxycarbonyl-N-methylaminoacetonitrile. This protected nitrile (11.5 g; 0.56 mol) was dissolved in a mixture of ethanol (25 ml) and ether (30 ml) and cooled to 0° C. Anhydrous HCl was bubbled through the reaction for 20 minutes, maintaining the temperature below 5° C. After stirring an additional hour at 0° C., the reaction was diluted with 200 ml of ether. The white solid which separated was filtered, washed with ether and dried to afford the product, m.p. 119°–121° C.

Step B: Preparation of 4,5-dihydro-2-(N-benzyloxycarbonyl-N-methylaminomethyl)-1H-imidazole hydrochloride Ethyl N-benzyloxycarbonyl-N-methylaminoacetimidate hydrochloride (10 g; 34.9 mmol) was added in portions to a solution of ethylenediamine (2.1 g; 34.9 mmol) in 50 ml of ethanol, maintaining the temperature below 5° C. After stirring the reaction an additional hour at 0° C., a solution of HCl (1.27 g) in 50 ml EtOH was added at a rate such that the temperature did not exceed 5° C. The reaction was then diluted with 250 ml of ethanol and heated at 40° C. for 1.5 hours. Ammonium chloride was removed by filtration and the warm filtrate was concentrated to a cloudy oil. Addition of 100 ml of isopropanol resulted in the separation of more ammonium chloride which was filtered off. Concentration of the filtrate afforded the product as a glassy solid.

Step C: Preparation of 2-(N-methylaminomethyl)-4,5-dihydro-1H-imidazole dihydrobromide A solution of 4,5-dihydro-2-(N-benzyloxycarbonyl-N-methylaminomethyl)imidazole hydrochloride (2.0 g) in 2 ml glacial acetic acid was added dropwise to 10 ml of a 30% solution of HBr in acetic acid. After stirring 0.5 hour the reaction was diluted gradually with 15 ml of ether. The mixture was then stirred 24 hours at ambient temperature. The product separated as a white solid which was collected on a filter, washed with ether, and dried. The yield was 1.97 g, m.p. 181°–183° C.

Step D: Preparation of N-((4,5-dihydro-1H-imidazol-2-yl)methyl)-N-methyl-8-aminoimidazo[1,2-a]pyrazine hydrogen oxalate A solution of sodium isopropoxide was prepared by adding sodium hydride (288 mg of a 50% oil dispersion, 6 mmol) to 30 ml of isopropanol. 2-Methylaminomethyl-4,5-dihydro-1H-imidazol-2-yl dihydrobromide (825 mg; 3 mmol) was added to the cooled solution and the reaction mixture was stirred 15 minutes at ambient temperature. 8-Chloroimidazo[1,2-a]pyrazine was then added and the reaction mixture was heated at reflux for 18 hours. After evaporating the solvent, the residue was chromatographed over silica gel, eluting with 10% MeOH/CHCl$_3$ saturated with ammonia. The crude product was treated with oxalic acid to obtain a crystalline salt which was recrystallized from isopropanol to afford the product, m.p. 154°–156° (dec).

EXAMPLE 5

| Pharmaceutical Formulation | Mg/Capsule |
|---|---|
| Active Ingredient | 6 |
| Starch | 87 |
| Magnesium stearate | 7 |

The active ingredient, starch and magnesium stearate are blended together. The mixture is used to fill hard shall capsules of a suitable size at a fill weight of 100 mg per capsule.

What is claimed is:

1. The compound of structural Formula I:

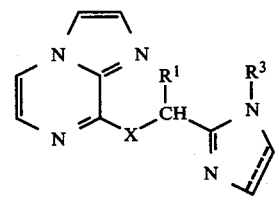

of a pharmaceutically acceptable salt thereof, wherein X is

—S—, >SO, >SO$_2$ or —O—; and R$^1$, R$^2$ and R$^3$ are independently hydrogen or C$_{1-3}$alkyl, and the dotted line is an optional double bond.

2. The compound of claim 1 wherein X is —S— or a pharmaceutically acceptable salt thereof.

3. The compound of claim 2 wherein R$^1$ and R$^3$ are both hydrogen.

4. An antihypertensive pharmaceutical formulation comprising a pharamaceutical carrier and an effective amount of the compound of claim 1.

5. The formulation of claim 4 wherein X is —S—, or a pharmaceutically acceptable salt thereof.

6. The formulation of claim 5 wherein R$^1$ and R$^3$ are both hydrogen.

7. A method of treating hypertension comprising the administration to a patient in need of such treatment of an effective amount of the formulation of claim 4.

8. The method of claim 7 wherein X is —S—, or a pharmaceutically acceptable salt thereof.

9. The method of claim 7 wherein R$^1$ and R$^3$ are both hydrogen.

* * * * *